United States Patent [19]
So et al.

[11] Patent Number: 5,909,449
[45] Date of Patent: Jun. 1, 1999

[54] MULTIBIT-PER-CELL NON-VOLATILE MEMORY WITH ERROR DETECTION AND CORRECTION

[75] Inventors: Hock C. So, Redwood City; Sau C. Wong, Hillsborough, both of Calif.

[73] Assignee: Invox Technology, Campbell, Calif.

[21] Appl. No.: 08/924,909

[22] Filed: Sep. 8, 1997

[51] Int. Cl.$^6$ ....................... G06F 11/00
[52] U.S. Cl. ....................... 371/21.4
[58] Field of Search ............ 371/21.4, 21.1, 371/21.2, 21.6, 10.2; 365/230.03, 225.7, 226, 227

[56] References Cited

U.S. PATENT DOCUMENTS

4,964,079  10/1990  Devin ........................ 365/168
5,689,465  11/1997  Sukegawa et al. ............ 371/10
5,751,639   5/1998  Ohsawa ....................... 365/227

*Primary Examiner*—Vincent P. Canney
*Attorney, Agent, or Firm*—Skjerven, Morrill, MacPherson, Franklin & Friel; David T. Millers

[57] ABSTRACT

A multilevel non-volatile memory divides the suitable threshold voltages of memory cells into ranges corresponding to allowed states for storage of data and ranges corresponding to forbidden zones indicating a data error. A read process in accordance automatically checks whether a threshold voltage is in a forbidden zone. In alternative embodiment, a refresh process includes reprogramming the threshold voltage into an allowed state or in the case of a flash memory, reading a sector of the memory, saving data from the sector in a buffer, erasing the sector, and rewriting the data from the buffer back in the sector. Refresh process for the non-volatile memory can be perform in response to detecting a threshold voltage in a forbidden zone, as part of a power-up procedure for the memory, or periodically with a period on the order of days, weeks, or months.

16 Claims, 5 Drawing Sheets

MULTIBIT-PER-CELL NON-VOLATILE MEMORY WITH ERROR DETECTION AND CORRECTION

BACKGROUND

1. Field of the Invention

This invention relates to non-volatile semiconductor memory and more specifically to circuits and methods for detecting and correcting data errors in a memory storing multiple bits per memory cell.

2. Description of Related Art

Conventional electrically erasable non-volatile semiconductor memories such as E²PROMs and flash memories have memory cells that include transistors with programmable threshold voltages. For example, a floating gate transistor or a split gate transistor has a threshold voltage that is programmed or erased by charging or discharging a floating gate located between a control gate and a channel in the transistor. The amount of charge on the floating gate of the transistor determines the voltage that must be applied to the control gate to cause charge carrier inversion in the underlying channel and therefore determines the threshold voltage of the transistor. Data is written in such memory cells by charging or discharging the floating gates of the memory cells to achieve threshold voltages corresponding to the data.

A binary memory stores one bit of data per memory cell. Accordingly, floating gate transistors in binary memory cells have two distinguishable states, a high threshold voltage state and a low threshold voltage state. Any memory cell having a threshold voltage above a cut-off threshold voltage value is in the high threshold voltage state and stores a bit value, 1 or 0, that corresponds to the high threshold state. Memory cells having threshold voltages below the cut-off are in the low threshold voltage state and store the bit value, 0 or 1, corresponding to the low threshold voltage state.

A multilevel memory stores multiple bits per memory cell. Accordingly, a range of threshold voltages for a memory cell is divided into a number of states corresponding to the possible multibit data values stored in the memory cell. For example, a memory that stores two bits of data per memory cell has a range of suitable threshold voltages for memory cells that is divided into four states. A first state includes threshold voltages below a first cut-off. A second state includes threshold voltages between the first cut-off and a second cut-off. A third state includes threshold voltages between the second cut-off and a third cut-off, and a fourth state includes threshold voltages above the third cut-off.

A concern in non-volatile semiconductor memory is drift or unintended changes in the threshold voltages of memory cells. For example, over time, charge tends to leak from the floating gates of memory cells and change the threshold voltages of the cells. Charge leakage decreases the threshold voltage of an N-channel memory cell. Alternatively, a floating gate or an insulator surrounding the floating gate can collect or trap charge and increase the threshold voltage of a cell. Further, operation of the memory, for example, programming or reading stresses memory cells not being accessed and can change threshold voltages. Changes in the threshold voltage are a problem because the state of the memory cell and the data value stored in the memory cell can change and create a data error. Such data errors are intolerable in many memory applications. The problem is worse for multilevel memories than for binary memories because the range of threshold voltages corresponding to a particular state is typically smaller in a multilevel memory which makes changes in the state of the multilevel memory cell more likely.

Multilevel memories that are resistant to data errors are sought.

SUMMARY

In accordance with the invention, a range of possible threshold voltages for a memory cell in a multilevel memory is divided into allowed states associated with data values and forbidden zones between the allowed states. A memory cell being written is programmed into an allowed state. Subsequent reading of the memory cell indicating that the threshold voltage of the memory cell is in a forbidden zone indicates that the threshold voltage of the memory cell has changed. A memory cell with a threshold voltage in a forbidden zone can be flagged as a data error or corrected by increasing or decreasing the threshold voltage to an adjacent allowed state. One specific embodiment of the invention is a flash memory that presumes charge loss in the memory cells and programs the threshold voltage of a memory cell up to the next allowed state when the memory detects that the threshold voltage of the memory cell is in a forbidden zone. Alternatively, the data error can be corrected by saving the data value in a buffer while the memory cell containing the error is erased and then programmed with the correct data value.

In accordance with another aspect of the invention, a non-volatile memory performs a refresh cycle in which memory cells are read and threshold voltages of the memory cells are reprogrammed to an allowed state. In a flash EPROM, the refresh cycle can refresh data in a single sector or an entire memory array. In alternative embodiments, the refresh cycle is triggered by external circuit attached to a monolithic integrated circuit memory or is self-triggered in the memory. Refreshes may be performed at periodic intervals of operation, as part of a power-up procedure for the memory, or transparently during each read operation performed by the memory.

According to a further aspect of the invention, adjacent states (i.e., ranges of threshold voltages) for a multilevel memory cell are mapped to data values using gray coding or another coding system instead of a direct monotonic mapping from threshold voltages to data values. With such coding, a drift from one threshold voltage state to an adjacent threshold voltage state causes only a single bit error. Such single bit errors can be detected and corrected using error correction codes. The gray coding of allowed states can be used with or without forbidden zones between the coded states and/or refresh cycles to correct stored data.

BRIEF DESCRIPTION OF THE DRAWINGS

Use of the same reference symbols in different figures indicates similar or identical items.

DETAILED DESCRIPTION OF THE PREFERRED EMBODIMENTS

Figure 1:
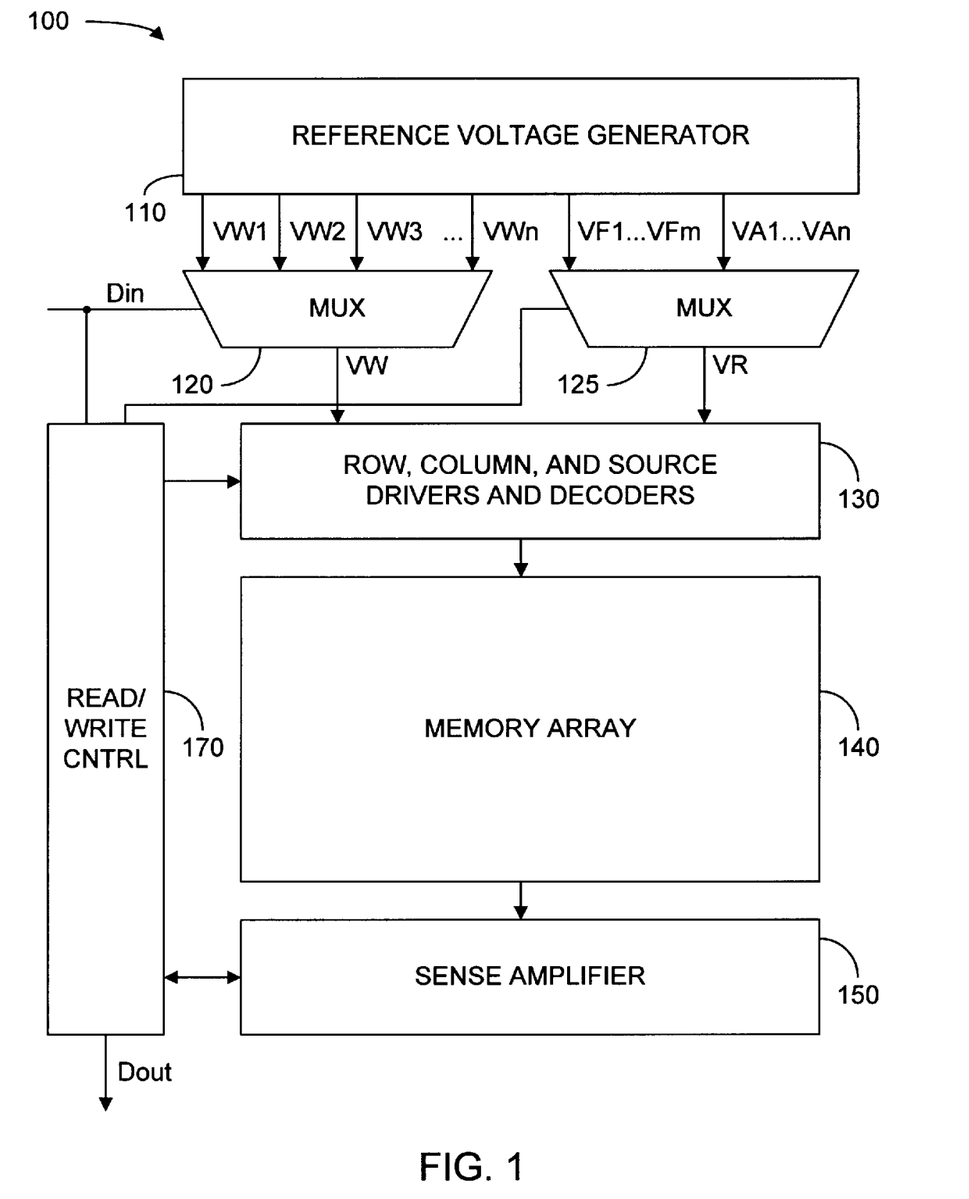
FIG. 1 shows a block diagram of a multilevel memory in accordance with an embodiment of the invention.

A multilevel memory in accordance with an embodiment of the invention partitions a range of threshold voltages of a memory cell into a set of allowed states that correspond to data values that can be stored in the memory cell and a set of forbidden zones. The allowed states are separated from each other by forbidden zones so that if the threshold voltage of a memory cell drifts it must cross through a forbidden zone before reaching another allowed state. A memory cell detected as having a threshold voltage in one of the forbidden zones indicates a data error which can be automatically corrected during a read or reported as an error for subsequent correction and refresh procedure. FIG. 1 illustrates a multilevel memory 100 in accordance with an embodiment of the invention. Memory 100 includes a memory array 140. In an exemplary embodiment of the invention, memory 100 is a flash EPROM, and array 140 includes hundreds or thousands of rows or columns of N-channel floating gate transistors (memory cells) organized into independently erasable sectors. Each row of memory cells has control gates coupled to a row line for the row, and each column of memory cells has drains coupled to a column line for the column. Each erasable sector has a source line coupled to the sources of memory cells in the sector. Row, column, and source drivers and decoders 130 are coupled to memory array 140 and generate voltages that are applied to selected row, column, and source lines in memory array 140 for erase, write, and read operations. For an erase, drivers and decoders 130 apply appropriate voltages to the memory cells in a sector to cause Fowler-Nordheim tunneling that removes electrons from the floating gates and reduces the threshold voltage of the memory cells in the sector. For a write operation, drivers and decoders 130 apply programming voltages to the row, column, and source lines coupled to a target memory cell to cause channel hot electron injection that increases the threshold voltage of the target memory cell to a level indicating a data value being written. As will be understood, applications of the invention are not limited to flash EPROM of the exemplary embodiment but can be employed in a variety of memory architectures including but not limited to EPROM, $E^2$PROM, and flash $E^2$PROM.

A read/write control circuit 170 controls writing to a target memory cell in memory array 140. For a write, an input digital data signal Din representing a multibit value to be written to the target memory cell is a select signal for a multiplexer 120. Signal Din is restricted to the number of bits that can be written to a single memory cell. Data values containing more bits than can be stored in a single memory cell may be split into parts containing the number of bits, e.g., 2, 3, 4 . . . bits, that can be stored in a single memory cell so that the parts can be written sequentially to memory cells using the circuitry shown in FIG. 1 or in parallel using parallel circuits (not shown.) Multiplexer 120, which is coupled to a reference voltage generator 110, selects one of input reference signals VW1 to VWn, where n is the number of possible data values that can be stored in a memory cell. (For example, n is sixteen ($2^x$) for memory storing 4-bits (x-bits) per memory cell.) Multiplexer 120 generates an analog signal VW to drivers and decoders 130 to indicate the value being written.

Figure 2A:
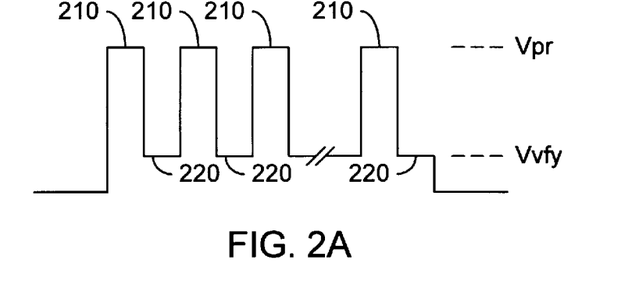
FIGS. 2A and 2B respectively show a row line voltage and a column line voltage during a write operation in the memory of FIG. 1.
Figure 2B:
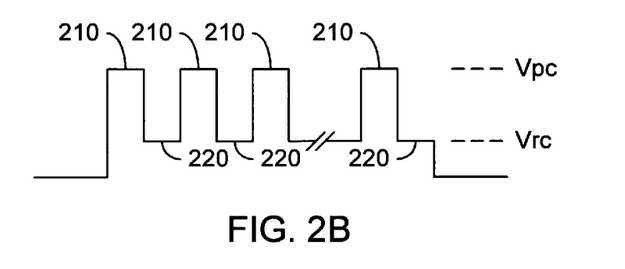

The write process proceeds as illustrated in FIGS. 2A and 2B. In particular, during a series of programming cycles 210, drivers and decoders 130 generate and apply programming voltages Vpr and Vpc to the row and column lines of a target memory cell while grounding the source line of the sector containing the target cell. In the exemplary embodiment, programming voltage Vpr is between 7 and 11 volts and depends on signal VW. Drivers and decoders 130 may include, for example, a row line driver containing voltage shifter or amplifier having signal VW as an input signal and voltage Vpr as an output signal. Alternatively, voltage Vpr may be a fixed voltage, independent of signal Vin. A conventional row decoder applies voltage Vpr to the row line coupled to the target memory cell. A conventional column decoder applies voltage Vpc to the drain of the target memory cell during programming cycles 210. Voltage Vpc is typically about 6 volts or whatever voltage is required to increase the threshold voltage of the target memory cell by channel hot electron (CHE) injection of electrons into the floating gate of the target memory cell. Alternative embodiments of the invention using, for example, $E^2$PROM technology program memory cells by tunneling instead of CHE injection.

Verify cycles 220 are performed between programming cycles 210 to determine whether the threshold voltage of the target memory cell has reached the desired level. During each verify cycle, drivers and decoders 130 apply to the control gate of the target memory cell a voltage Vvfy which depends on (or is equal to) voltage VW (i.e., one of reference voltages VW1 to VWn), grounds the source lines, and applies a read voltage Vrc to the column line of the target memory cell. A sense amplifier 150 senses whether the target memory cell conducts. If the target memory cell conducts during a verify cycle 220, the threshold voltage of the memory cell is less than voltage Vvfy, and read/write control 170 starts another programming cycle 210 to further increase the threshold voltage. If the target memory cell does not conduct during a verify cycle 220, the threshold voltage has exceeded (but is about equal to voltage Vvfy), and read write control 170 stops further programming cycles 220.

Figure 3A:
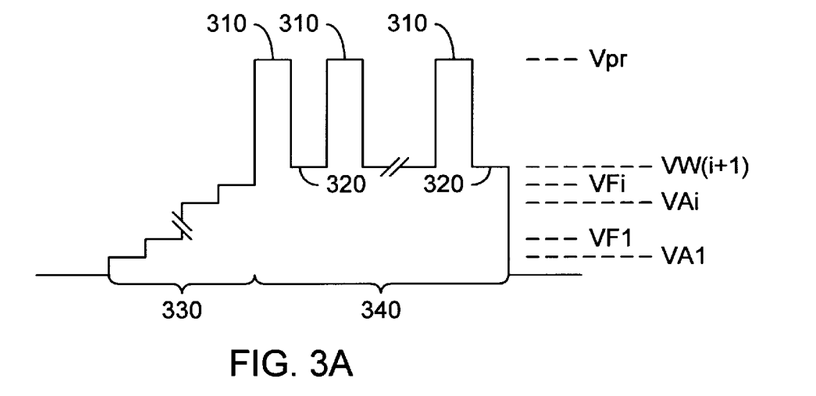
FIGS. 3A and 3B respectively show a row line voltage and a column line voltage during a read/refresh operation in the memory of FIG. 1.
Figure 3B:
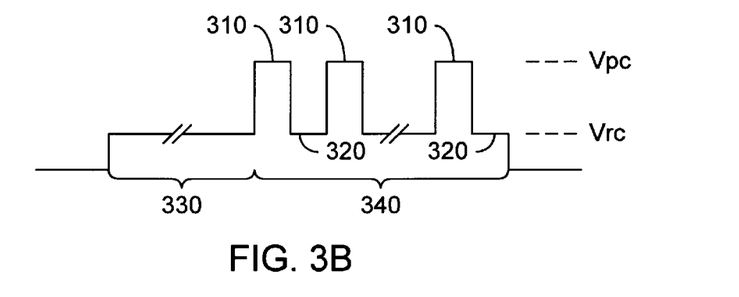
Figure 4A:
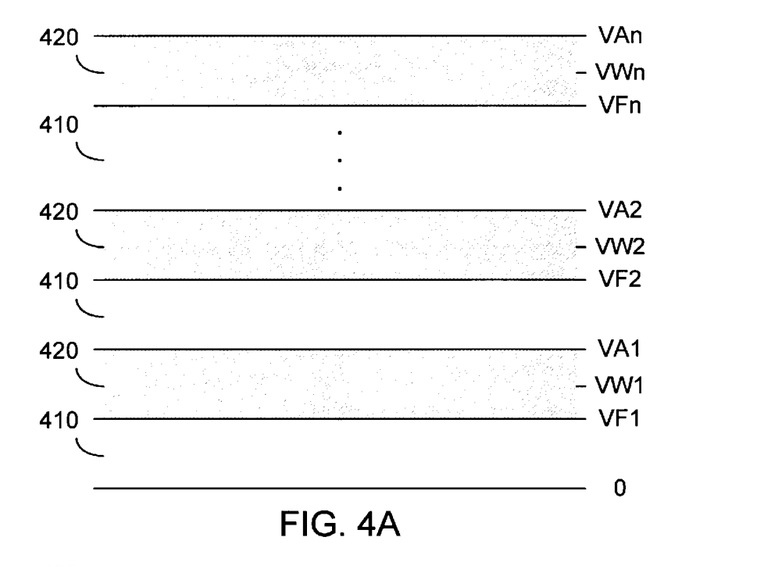
FIGS. 4A and 4B show partitions of threshold voltage ranges into allowed states and forbidden zones in accordance with an embodiment of the invention.

Read/write control 170 also controls read and refresh processes in accordance with an embodiment of the invention. FIGS. 3A and 3B respectively show a row line voltage and a column line voltage during an exemplary combined read/refresh process performed on a target memory cell. During a read stage 330 of the read/refresh process, drivers and decoders 130 ground the source lines, apply a constant read voltage Vrc (typically about 1 to 2 volts) to the column line coupled to the target memory cell, and apply a series of reference voltages from reference voltage generator 110 to the row line (and therefore the control gate) of the target memory cell. For each reference voltage applied to the row line during read stage 330, sense amplifiers 150 sense whether the target memory cell conducts. The applied reference voltages during read stage 130 indicate the bounds of allowed threshold voltage states and of forbidden threshold voltage zones such as illustrated in FIG. 4A. In FIG. 4A, reference voltages VF1 to VFm mark the upper bounds of forbidden zones 410 and the lower bounds of allowed threshold voltage states 420. Reference voltages VA1 to VAn mark the upper bounds of allowed threshold states 420 and the lower bounds of forbidden zones 410. Each of the reference voltage levels VW1 to VWn are within an associated one of allowed states 420 so that a write operation ends with a threshold voltage of a target memory cell being in the allowed state 420 associated with the reference voltage VW. To provide the desired reference voltages as shown in FIG. 4A (or 4B), reference voltage generator 110 may contain a voltage source coupled to series connected resistive elements with taps between the resistive elements for the reference voltages VW1 to VWn, VF1 to VFm, and VA1 and VAn.

During read stage 330, read/write control 170 uses multiplexer 125 to select reference voltages applied to through drivers and decoders 130 to the row line coupled to the target memory cell. Reference voltages starting with lowest reference voltage (voltage VF1 in FIG. 4A) are sequentially applied in order of increasing voltage until sense amplifier 150 senses that applied voltage VR causes the target memory cell to conduct. Thus, at the end of read stage 330, voltage VR is upper bound of the allowed state or forbidden zone containing the threshold voltage of the target memory cell. An alternative read process to that shown in FIGS. 3A and 3B starts at the maximum reference voltage VAn and proceeds in order of decreasing threshold voltage to find a lower bound of the allowed state or forbidden zone containing the threshold voltage of the target memory cell. Yet another read process starts at a reference voltage in the middle of the range of reference voltages and identifies which half (upper or lower) of the range contains the target threshold voltage. (If the memory cell conducts when the middle reference value is applied, the threshold voltage of the target memory cell is in the lower half. Otherwise, the threshold voltage of the target memory cell is in the upper half.) Second and if necessary third and subsequent reference voltages applied to the control gate are in the middle of the range previously identified as containing the threshold voltage of the target memory cell. Sensing for these threshold voltages identifies which quarter, eighth, or smaller division of the threshold voltage range contains the threshold voltage of the target cell. When the division identified is a single allowed state or forbidden zone, the reference voltage that is just above the threshold voltage of the target memory cell is identified. An advantage of the last read process is an on-average decrease in the number of reference voltages applied and sensed from $2^{x-1}$ to x where x is the number of bits stored per memory cell. Thus, the last read process provides better average performance for memory storing more than two bits per memory cell.

Voltage VR at the end of read stage 330 indicates the upper bound of either an allowed state or a forbidden zone containing the threshold voltage of the target memory cell. Read/write control 170 generates a multibit digital data signal Dout based on the bound that voltage VR identifies. If voltage VR at the end of read stage 330 is an upper bound of an allowed state, signal Dout indicates the multibit value associated with that state. If voltage VR is an upper bound of a forbidden zone, value Dout indicates the multibit value associated with the allowed state just above the forbidden zone containing the threshold voltage of the memory cell. Thus, this read process assumes that the threshold voltage of the target memory drifted down which is the most common type of change in threshold voltage for N-channel floating gate transistors. If voltage VR is the upper bound of an allowed threshold voltage state at the end of read stage 330, the read/refresh process is complete. No refresh is required. However, if as in FIGS. 3A, voltage VR is the upper bound of a forbidden zone, a refresh stage 340 of the read/refresh process begins.

During refresh stage 340, programming cycles 310 and verify cycles 320 raise the threshold voltage of the target memory cell to the next higher threshold voltage state. In the particular example of FIGS. 3A and 3B, voltage VR is equal to reference voltage VF1 at the end of read stage 330, and signal Dout identifies the multibit value corresponding to the next greater allowed level and to reference voltage VW(i+1). Read/write control 170 feeds signal Dout back to multiplexer 120 which sets voltage VW equal to the reference voltage VW(i+1). Thus, during programming cycles 310 and verify cycles 320, programming voltage Vpr and verify voltage Vvfy are appropriate for the value being refreshed. As in the write process described above, programming cycles 310 continue until a verify cycle 320 indicates that the threshold voltage of the target cell has reached the level of reference voltage VW(i+1) after which refresh stage 340 is complete.

Figure 5:
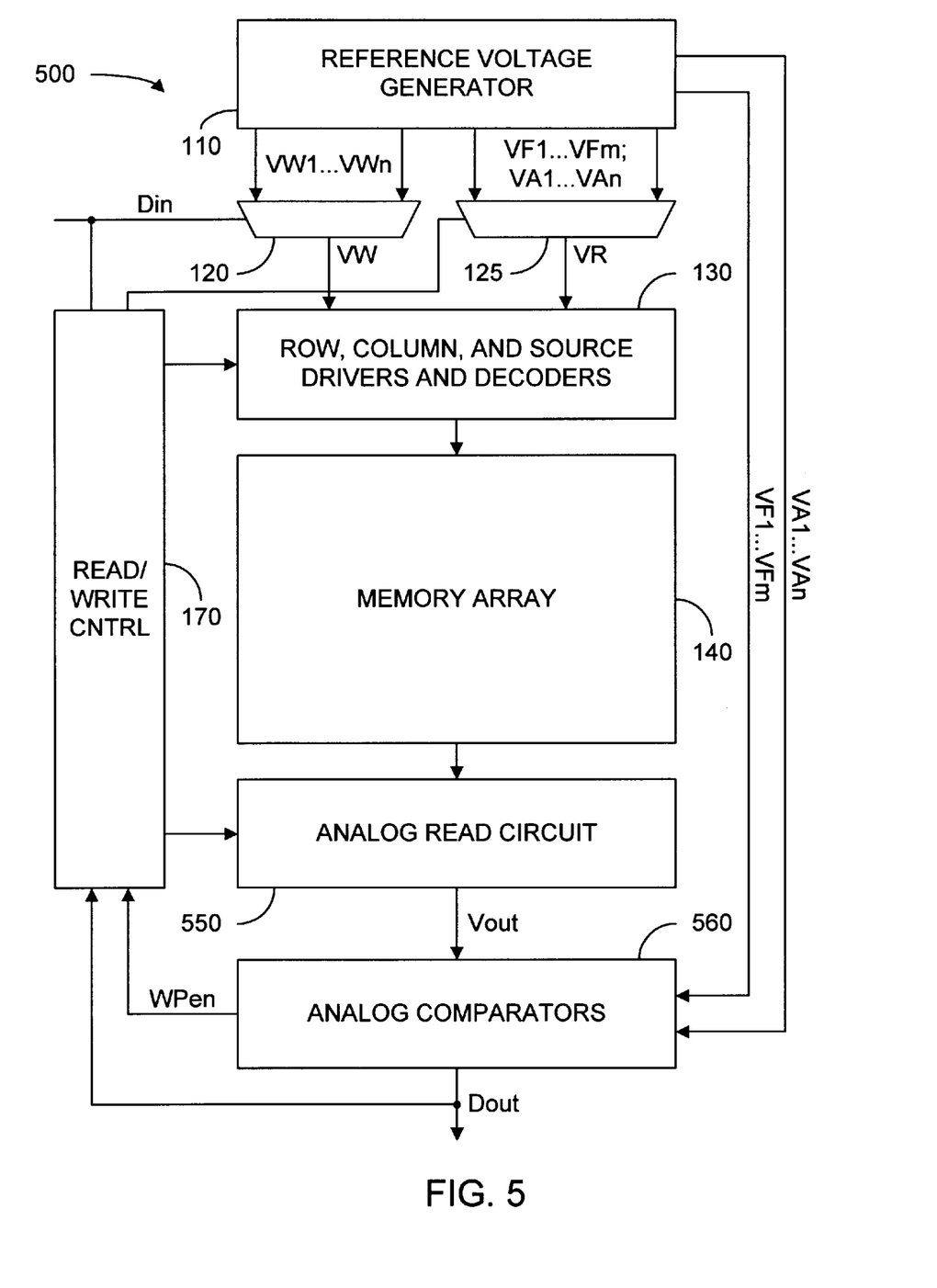
FIG. 5 shows a block diagram of a multilevel memory in accordance with another embodiment of the invention.

FIG. 5 shows an alternative multilevel non-volatile memory 500 in accordance with an embodiment of the invention. Memory 500 differs from memory 100 of FIG. 1 primarily in that a read uses an analog read circuit 550 and comparators 560, not sense amplifiers 150. In particular, instead of repeatedly sensing whether the target memory cell conducts when a series of different reference voltages is applied to the control gate of the memory cell, analog read circuit 550 generates an analog voltage Vout that indicates the threshold voltage of the target memory cell. In an alternative embodiment, analog read circuit generates a signal having a current that indicates the threshold voltage of a target memory cell. U.S. patent application Ser. No. 08/585,072, entitled "Read Circuits for Analog Memory Cells"; U.S. patent application Ser. No. 08/622,333, entitled "Feedback Loop for Threshold Voltage Measurement"; and U.S. patent application Ser. No. 08/622,332, entitled "Read Circuit that uses a Coarse-to-Fine Search when Reading the Threshold Voltage of a Memory Cell" describe suitable analog read circuits and are incorporated by reference herein in their entirety. Analog comparators 560 operate in parallel to compare voltage Vout to reference voltages VA1 . . . VAn and VF1 . . . VFN. From the results of the comparisons, logic (not shown) coupled to analog comparators 150 determines which is the smallest reference voltage greater than voltage Vout and generates digital output signal Dout. The architecture of memory 500 typically provides faster reads than memory 100 if generating signal Vout is faster than applying as series of reference voltages.

Alternatively, analog comparators 560 include one comparator or fewer comparators than there are references voltages VA1 . . . VAn and VF1 . . . VFN, and the comparator or comparators sequentially compare voltage Vout to each references voltages VAI . . . VAn and VF1 . . . VFN. Any sequence of comparisons can be made. For example, comparisons searching for the nearest reference voltage can start from a highest, lowest, or middle reference voltage and proceed until the range containing Vout is found. This embodiment of the invention can decrease circuit size and cost but increases the read time.

Figure 4B:
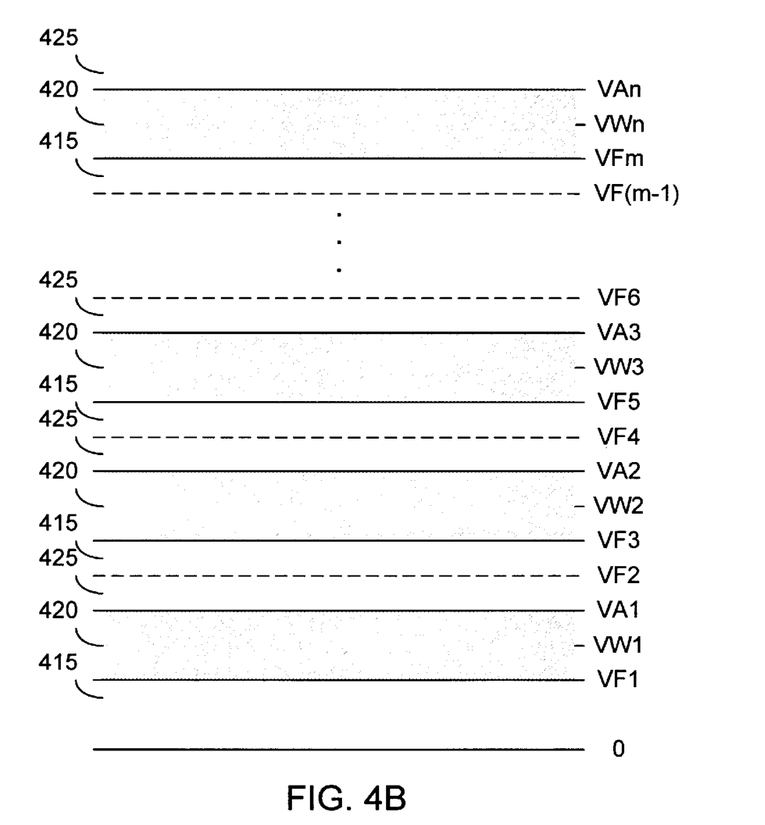

The write/refresh process described above assumes that a threshold voltage in a forbidden zone indicates a memory cell that leaked charge which decreased the threshold voltage of the memory cell. However, threshold voltages can also increase as the result of charge trapping in a floating gate or in the insulator surrounding the floating gate. FIG. 4B illustrates reference voltage levels VF1 to VFm that define two forbidden zones 415 and 425 between each adjacent pair of allowed states 420. Each forbidden zone 415 is just below an adjacent allowed state 420. Each forbidden zone 425 is just above an adjacent allowed state 420. In accordance with this embodiment of the invention, a data error that occurs when a memory cell has a threshold voltage in one of forbidden zones 415 is presumed to result from charge loss from a memory cell originally in the adjacent higher allowed state 420. Thus, read/write control 170 decodes a threshold voltage in a forbidden zone 415 as data values corresponding to the next higher allowed state 420. A threshold voltage in one of forbidden zones 425 is presumed to result from charge trapping or another mechanism increasing the threshold voltage from the adjacent lower allowed state 420. Read/write control 170 decodes a threshold voltage in a forbidden zone 425 as data values corresponding to the next lower allowed state 420.

Figure 6:
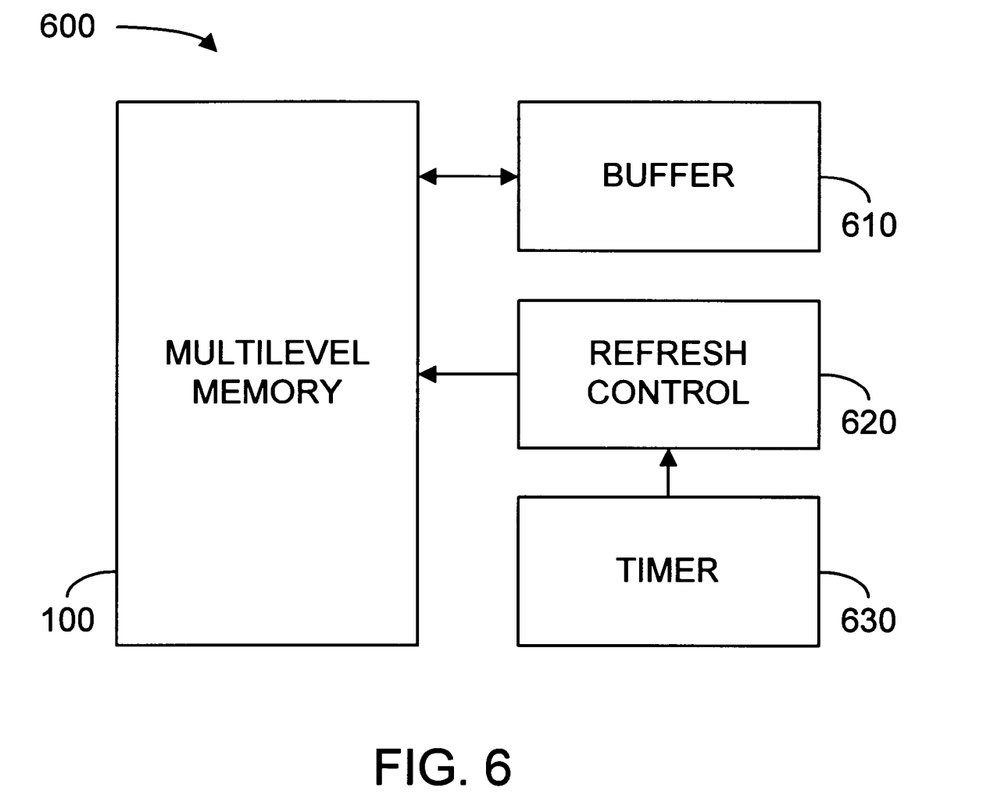
FIG. 6 shows a block diagram of a multilevel non-volatile memory system with refresh circuits in accordance with an embodiment of the invention.

Threshold voltages in forbidden zones 415 can be corrected by programming the memory cell up to the next allowed state. Similarly, if a memory architecture provides a method for individual erasing or reducing the threshold voltage of a single memory cell, a threshold voltage in a forbidden zone 425 can be lowered to the next lower allowed state. However, a typical flash memory architecture erases sectors as a unit and does not provide a mechanism for erasing or reducing the threshold voltage of individual memory cells. In such flash architectures, a sector containing a data error can be marked as requiring a refresh. Special memory cells in the array or a separate register can be used to identify the data sectors marked for a refresh. FIG. 6 illustrates a system 600 capable of performing scheduled or delayed refreshes of sectors. In system 600, a read detecting a data error caused when a memory cell is in a forbidden zone signals a refresh control 620 that can be an on-chip component integrated with memory 100 or an off-chip component. The refresh for a data sector marked as containing a data error need not be immediate. Instead refresh control 620 can wait for a period of inactivity of memory 100 before initiating a refresh of the marked sector.

To perform a refresh of an erasable sector, refresh controller 620 reads data from the sector and temporarily stores the data in a buffer 610 while the data sector is erased. Buffer 610 can be on-chip or off-chip volatile memory such as SRAM or DRAM or non-volatile memory. Refresh control 620 rewrites data from buffer 610 to the sector after the erase. During the refresh of a data sector, refresh control 620 can perform arbitration to avoid accessing of a sector being erased. For example, memory 100 may be flagged as temporarily unavailable; or alternatively, refresh control 620 can reroute an access, particularly a read, to buffer 610.

System 600 also includes a timer 630 for systematic memory refreshes and delaying flagged refreshes until a convenient time. In alternative embodiments of the invention, timer 630 is on-chip or is an off-chip component. As described above, a typical refreshes affects a sector but an entire memory can be refreshed sector by sector if desired. Such refreshes can keep data accurately stored in nonvolatile memory for extended periods of time even if the data is not otherwise read periodically. In one embodiment of the invention, memory refreshes are periodic with a period shorter than the time required for a non-defective memory cell to drift from one allowed state, across a forbidden zone to another allowed state or a forbidden zone corresponding to another allowed state. Such periods are typically be on the order of weeks or months for current non-volatile memory but more frequent refreshes having a period of on the order of a day or less can be used. Because of the long intervals between refreshes, periodic memory refreshes may be scheduled for times when use of the memory is less likely. Selection of the time for a refresh can be selected according to the time of the day or the day of the week to select a time when memory access is unlikely, for example, midnight on a Sunday. Refresh control 620 can also monitor memory access to select and further delay a refresh until detecting a suitably long period of memory inactivity. The last date and time of a refresh can be stored on-chip and checked periodically when the memory is powered. Additionally or alternatively, refresh control 620 can conduct a full or partial refresh of memory 100 as part of a power-up procedure for memory 100.

As another aspect of the invention, a mapping between allowed threshold voltage states and digital values maps adjacent threshold voltage levels to multibit values that differs only in a single bit. Accordingly, the threshold voltage of a memory cell drifting from one threshold voltage state to an adjacent state causes a single bit error. In contrast, for conventional data coding, which monotonically maps threshold voltages states with increasing (or decreasing) threshold voltage to sequentially increasing binary values, a memory cells threshold voltage drifting a single state can cause a multibit error.

Table 1 illustrates two data coding schemes for a multi-level memory that stores one 4-bit value per memory cell. To store a 4-bit value in a memory cell, sixteen allowed states are allocated in the range of possible (or suitable) threshold voltages for the memory cell. For Table 1, a threshold voltage ranging between 1 and 5 volts is partitioned into sixteen allowed states designated levels 1 to 16.

TABLE 1

16-bit Linear and Gray Coded States

| LEVEL | THRESHOLD VOLTAGE | LINEAR CODING | GRAY CODING |
|---|---|---|---|
| 1  | 1.0–1.2 V | 0000 | 0000 |
| 2  | 1.3–1.5 V | 0001 | 0001 |
| 3  | 1.5–1.7 V | 0010 | 0011 |
| 4  | 1.8–2.0 V | 0011 | 0010 |
| 5  | 2.0–2.2 V | 0100 | 0110 |
| 6  | 2.3–2.5 V | 0101 | 0111 |
| 7  | 2.5–2.7 V | 0110 | 0101 |
| 8  | 2.8–3.0 V | 0111 | 0100 |
| 9  | 3.0–3.2 V | 1000 | 1100 |
| 10 | 3.3–3.5 V | 1001 | 1101 |
| 11 | 3.5–3.7 V | 1010 | 1111 |
| 12 | 3.8–4.0 V | 1011 | 1110 |
| 13 | 4.0–4.2 V | 1100 | 1010 |
| 14 | 4.3–4.5 V | 1101 | 1011 |
| 15 | 4.5–4.7 V | 1110 | 1001 |
| 16 | 4.8–5.0 V | 1111 | 1000 |

The linear coding according of Table 1 maps threshold voltage levels 1 to 16 in order of increasing threshold voltage to sequentially increasing binary values 0000 to 1111. With linear coding, if the threshold voltage of a memory cell is programmed to threshold voltage level 9 but drifts down to threshold voltage level 8, a 4-bit error occurs. In contrast, for the gray coding of Table 1, a threshold voltage drifting to an adjacent allowed state causes only a single bit error.

As a further aspect of the invention, error correction codes can be generated and stored for a section, row, column, or other part of a memory and used to correct data errors. In particular, when a threshold voltage is observed in a forbidden zone, an error correction code generated when data was written can be used to determine the correct allowed threshold voltage state for a memory cell. The error correction codes can identify the correct threshold voltage states when reading or refreshing memory cells. The gray coding of Table 1 is well suited to use with error correction codes since single bit errors are typically easier to correct with error correction codes than are multiple bit errors.

The gray coding process of Table 1 can be varied in a variety of ways. For example, many different mappings which provide a series of values where adjacent values differ by a single bit are possible. Such mappings are not restricted to 4-bit data values but are known for any size of multibit data values. Also, although Table 1, describes allowed states which are separated from each other to provide forbidden zones between the allowed states, gray coding of multibit values in a memory cell is applicable to memories where the range of threshold voltages for a memory cell does not includes forbidden zones between the allowed states.

To implement the gray coding of Table 1 in memory array 100, multiplexer 120 implements the mapping between a 4-bit digital value Din as in column 4 of Table 1 to a voltage VW that is within a voltage range indicated in column 2 of Table 1. Read/write control 170 performs the reverse mapping from VR at the end of the read stage the associate digital value in column 4 of Table 1.

Although the invention has been described with reference to particular embodiments, the description is only an example of the inventions application and should not be taken as a limitation. In particular, even though much of preceding discussion was aimed at non-volatile memory including N-channel floating gate devices, alternative embodiments of this invention include other memory structures. For example, embodiments employing P-channel transistors are possible. In such embodiments, erasing and charge leakage increase the threshold voltage of a memory cell, and programming decreases the threshold voltages. Accordingly, variations in the read and write processes described above are required. Various other adaptations and combinations of features of the embodiments disclosed are within the scope of the invention as defined by the following claims.

We claim:

1. A non-volatile semiconductor memory comprising:

an array of memory cells;

drivers and decoders coupled to apply voltages to the array, as required to write to any memory cell in the array and to read any memory cell in the array, wherein each memory cell that stores data has a threshold voltage that identifies a multibit data value written in the memory cell;

a reference generator that generates first reference signals and second reference signals, wherein the first reference signals indicate bounds of ranges of threshold voltages allowed for the memory cells storing data, and the second reference signals indicate bounds of one or more ranges of threshold voltages forbidden for the memory cells storing data; and a control circuit coupled to control the drivers and decoders during a read process, the control circuit including logic that initiates a process to refresh a threshold voltage of a memory cell during a read process that detects the threshold voltage of the memory cell is in a range forbidden for memory cells storing data.

2. The non-volatile memory of claim 1, further comprising a timer that triggers a refresh operation by initiating reading of at least a portion of the memory array.

3. The non-volatile memory of claim 2, wherein the array, the drivers and decoders, the reference generator, the control circuit, the timer are parts of a monolithic integrated circuit.

4. The non-volatile memory of claim 2, further comprising a buffer coupled to temporarily store data from the portion of the memory array, during the refresh operation.

5. The non-volatile memory of claim 1, wherein the ranges of threshold voltages allowed for memory cells storing data are separated from each other by at least one range of threshold voltages forbidden for memory cells storing data.

6. A method for operating a non-volatile memory, comprising:

measuring a threshold voltage of a memory cell;

generating a multibit digital signal corresponding to the threshold voltage;

identifying whether the threshold voltage is in one of a first plurality of ranges of threshold voltages or in one of a second plurality of ranges of threshold voltages; and in response to the threshold voltage being in one of the first plurality of ranges of threshold voltages, changing the threshold voltage so that the threshold voltage is in one of the second plurality of ranges of threshold voltages.

7. The method of claim 6, wherein changing the threshold voltage changes the threshold voltage so that the threshold voltage is in a range that corresponds to the multibit digital signal.

8. The method of claim 6, wherein:

the second plurality of ranges of threshold voltages form a sequence of ranges ordered according to increasing maximum voltages of the ranges;

each range corresponds to a different multibit digital value; and the multibit digital value for each range differs by only one bit, from the multibit value for the range immediately preceding in the series.

9. The method of claim 6, wherein the steps of claim 6 are performed as part of a standard read operation for the memory.

10. A method for operating a non-volatile memory, comprising:

programming threshold voltages of memory cells in the non-volatile memory so that each memory cell has a threshold voltage in an allowed state associated with a multibit data value stored in the memory cell, wherein threshold voltages of the memory cells have a plurality of allowed states that are separated from each other by forbidden zones;

identifying a portion of the non-volatile memory that contains a memory cell with a threshold voltage in one of the forbidden zones; and refreshing the multibit data values stored in memory cells in the identified portion by reprogramming the threshold voltages.

11. The method of claim 10, wherein refreshing the multibit data values is performed in response to a signal from a timer.

12. The method of claim 11, wherein refreshing the multibit data values is performed periodically with a period greater than one day.

13. The method of claim 11, further comprising determining a time during which use of the memory is unlikely, wherein the timer schedules refreshing for that time.

14. The method of claim 10, wherein refreshing the multibit data values is performed as part of a power up procedure for the memory.

15. The method of claim 10, wherein the portion identified as containing a memory cell with a threshold voltage in one of the forbidden zones is a sector, and refreshing the multibit data values comprises:

reading data values from the sector;

storing the data values in a buffer;

erasing the sector; and writing the data values back in the sector.

16. The method of claim 10, wherein reading the data values comprises measuring the threshold voltage of the memory cell with the threshold voltage in one of the forbidden zones, wherein a data value read from that memory cell corresponds to an allowed state near the forbidden zone containing the threshold voltage of the memory cell.

\* \* \* \* \*